US011414460B2

(12) United States Patent
Heath

(10) Patent No.: US 11,414,460 B2
(45) Date of Patent: Aug. 16, 2022

(54) KRAS-SPECIFIC CAPTURE AGENTS, COMPOSITIONS, AND METHODS OF MAKING AND USING

(71) Applicant: Institute for Systems Biology, Seattle, WA (US)

(72) Inventor: James R. Heath, Seattle, WA (US)

(73) Assignee: INSTITUTE FOR SYSTEMS BIOLOGY, Seattle, WA (US)

( * ) Notice: Subject to any disclaimer, the term of this patent is extended or adjusted under 35 U.S.C. 154(b) by 0 days.

(21) Appl. No.: 16/933,679

(22) Filed: Jul. 20, 2020

(65) Prior Publication Data

US 2021/0032293 A1  Feb. 4, 2021

Related U.S. Application Data

(60) Provisional application No. 62/876,598, filed on Jul. 19, 2019.

(51) Int. Cl.
  *A61K 38/00*  (2006.01)
  *C07K 7/50*  (2006.01)

(52) U.S. Cl.
  CPC .............. *C07K 7/50* (2013.01); *A61K 38/00* (2013.01)

(58) Field of Classification Search
  CPC . A61K 38/00; C07K 7/50; C07K 7/06; G01N 33/5748
  See application file for complete search history.

(56) References Cited

U.S. PATENT DOCUMENTS

| | | | |
|---|---|---|---|
| 4,899,755 | A | 2/1990 | Lauffer |
| 5,021,556 | A | 6/1991 | Srinivasan |
| 5,075,099 | A | 12/1991 | Srinivasan |
| 5,183,653 | A | 2/1993 | Linder |
| 5,364,613 | A | 11/1994 | Sieving |
| 5,367,080 | A | 11/1994 | Toner |
| 5,387,409 | A | 2/1995 | Nunn |
| 5,474,756 | A | 12/1995 | Tweedle |
| 5,608,110 | A | 3/1997 | Ramalingam |
| 5,656,254 | A | 8/1997 | Ramalingam |
| 5,662,885 | A | 9/1997 | Pollak |
| 5,665,329 | A | 9/1997 | Ramalingam |
| 5,688,487 | A | 11/1997 | Linder |
| 5,720,934 | A | 2/1998 | Dean |
| 5,780,006 | A | 7/1998 | Pollak |
| 5,846,519 | A | 12/1998 | Tweedle |
| 5,849,261 | A | 12/1998 | Dean |
| 5,879,658 | A | 3/1999 | Dean |
| 5,886,142 | A | 3/1999 | Thakur |
| 5,976,495 | A | 11/1999 | Pollak |
| 6,093,382 | A | 7/2000 | Wedeking |
| 6,143,274 | A | 11/2000 | Tweedle |
| 2010/0009896 | A1 | 1/2010 | Agnew |
| 2016/0264627 | A1* | 9/2016 | Henning .................. A61P 35/00 |
| 2017/0319722 | A1* | 11/2017 | Agnew ............ C07K 14/70517 |

FOREIGN PATENT DOCUMENTS

| | | |
|---|---|---|
| WO | 1986006605 | 11/1986 |
| WO | 1991003200 | 3/1991 |
| WO | 1995003280 | 2/1995 |
| WO | 1995006633 | 3/1995 |
| WO | 1995028179 | 10/1995 |
| WO | 1995028967 | 11/1995 |
| WO | 1996003427 | 2/1996 |
| WO | 1996023526 | 8/1996 |
| WO | 1997036619 | 10/1997 |
| WO | 1998018496 | 5/1998 |
| WO | 1998018497 | 5/1998 |
| WO | 1998046612 | 10/1998 |
| WO | 9852618 | 11/1998 |
| WO | 1999017809 | 4/1999 |
| WO | 2003006620 | 1/2003 |
| WO | 2007050963 | 5/2007 |
| WO | 2009155420 A1 | 12/2009 |
| WO | 2012106671 | 8/2012 |
| WO | 2013009869 | 1/2013 |
| WO | 2013033561 | 3/2013 |
| WO | 2014074907 | 5/2014 |
| WO | 2014205317 | 12/2014 |
| WO | 2017176769 | 10/2017 |

(Continued)

OTHER PUBLICATIONS

Agnew, et al., "Iterative In Situ Click Chemistry Creates Antibody-like Protein-Capture Agents". Angew. Chem. Int. Ed. Engl., 48(27):4944-4948 (2009).

Alexander, et al., "Intracranial black-blood MR angiography with high-resolution 3D fast spin echo", Magn. Reson. Med., 40(2):298-310 (1998).

Altschul, et al.. "Gapped BLAST and PSI-BLAST: a new generation of protein database search programs", Nucleic Acids Res., 25(17):3389-402 (1997).

Baines, et al., "Inhibition of Ras for cancer treatment: the search continues", Future Med Chem., 3(14):1787-1808 (2011).

Bamford, et al., "The COSMIC (Catalogue of somatic Mutations in Cancer) database and website", British Journal of Cancer, 91(2):355-358 (2004).

Cheong, et al., "A patent review of IDO1 inhibitors for cancer", Expert Opinion on Theraveutic Patents, 28(4):317-330 (2018).

(Continued)

*Primary Examiner* — Aradhana Sasan
*Assistant Examiner* — Mercy H Sabila
(74) *Attorney, Agent, or Firm* — Pabst Patent Group LLP

(57) ABSTRACT

Disclosed are compounds, compositions, and methods involving cyclic peptides that can bind to KRAS (G12D) oncogenic protein. For example, disclosed are cyclic peptides that selectively bind KRAS (G12D) oncogenic protein. Also disclosed are methods of inhibiting KRAS (G12D) oncogenic protein in a cancer cell expressing KRAS (G12D) oncogenic protein. In some forms, the method comprises incubating the cancer cell with any one or more of the disclosed cyclic peptides. In some forms, the method comprises bringing into contact the cancer cell with any one or more of the disclosed cyclic peptides.

30 Claims, 5 Drawing Sheets

Specification includes a Sequence Listing.

(56) References Cited

FOREIGN PATENT DOCUMENTS

WO 2018064597 4/2018

OTHER PUBLICATIONS

Claverie, "Information enhancement methods for large scale sequence analysis", Comput. Chem., 17(2):191-201 (1993).
Coppock, et al., "Peptide-based protein capture agents with high affinity, selectivity, and stability as antibody replacements in biodetection assays", Optical Sensing 9107:106 (2014).
Corson, et al., "Design and applications of bifunctional small molecules: Why two heads are better than one", ACS Chem. Biol., 3(11):677-692 (2008).
Das, et al., "A General Synthetic Approach for Designing Epitope Targeted Macrocyclic Peptide Ligands", Angew. Chemie Int. Ed. Engl. 54(45):13219-24 (2015).
Downward, et al., "Targeting Ras Signaling Pathways in Cancer Therapy", Nature Reviews; Cancer, 3:11-22 (2003).
Edelman, et al., "Extracranial carotid arteries: evaluation with "black blood" MR angiography", Radiology, 177(1):45-50 (1990).
Farrow, et al., "Epitope-Targeting of Tertiary Protein Structure Enables Target-Guided Synthesis of a Potent in Cell Inhibitor of Botulinum Neurotoxin", Angew. Chemie Int. Ed. Engl. , 54 (24), 7114-7119(2015).
Goodrich, et al., "A quantitative study of ramped radio frequency, magnetization transfer, and slab thickness in three-dimensional time-of-flight magnetic resonance angiography in a patient population", Invest. Radiol., 31:323-32 (1996).
International Search Report for PCT application PCT/US2017/054546 dated Mar. 22, 2018.
International Search Report for PCT application PCT/US2020/033858 dated Oct. 12, 2020.
Iwata, et al., "A New, Convenient Method for the Preparation of 4-[18F] fluorobenzyl Halides", Applied Radiation and Isotopes, 52(1):87-92 (2000).
Lee, et al., "Rapid Microwave-Assisted CNBr Cleavaae of Bead-Bond Peptides", J. Comb. Chem., 10(6) 807-809 (2008).
Liu, e al., "99mTc-Labeled Small Peptides as Diagnostic Radiopharmaceuticals", Chem. Rev, 99(1):2235-2268 (1999).
Meyers and Miller, "Optimal alignments in linear space", Comp Applic. Biosci, 4(1):11-17 (1988).
Nag, et al., "A chemical epitope-targeting strategy for protein capture agents: The Serine 474 epitope of the Kinase Akt2", Angew . Chem. Int. Ed. Engl., 52(52):13975-13979 (2013).
Oh, et al., "Amphilic Bicyclic Peptides as cellular Delivery Agents", ChemMedChem, 9(11):2449-2453 (2014).
Ostrem, et al., "K-Ras (G12C) inhibitors allosterically control GTP affinity and effector interactions", Nature , 503(7477):548-51 (2013).
Poethko, et al., "Two-Step Methodology for High-Yield Routine Radiohalogenation of Peptides: 18F-Labeled RGD and Octreotide Analogs", The Journal of Nuclear Medicine, 4(5)5:692-902 (2004).
Röhrig et al., "Challenges in the Discovery of Indoleamine 2,3-Dioxygenase 1 (IDO1) Inhibitors", J. Med. Chem., (2015).
Schottelius, et al., "First 18F-Labeled Tracer Suitable for Routine Clinical Imaging of sst Receptor-Expressing Tumors Using Positron Emission Tomography", Clinical Cancer Research, 10:3593-3606(2004).
Schubbert, et al., "Hyperactive Ras in developmental disorders and cancer", Nature Reviews; Cancer, 7:295-308 (2007).
Son, et al., "New Cyclic Lipopeptides of the Inturin Class Produced by Saltern-Derived *Bacillus* sp. KCB14S006", Marine Drugs, 14(4):72 (2016).
Terpe, et al., "Overview of tag protein fusions: from molecular and biochemical fundamentals to commercial systems", Appl. Microbiol. Biotechnol, 60(5):523-533 (2003).
Toure, et al., "Small-Molecule PROTACS; New Approaches to Protein Degradation and Crews", Angew. Chem. Int. Ed., 55(6): 1966-1973 (2016).
Wilson, et al., "Reductive Amination of [18F]Fluorobenzaldehydes: Readiosyntheses of [2-18F]-and [4-18F] Fluorodexetimides." Journal of Labeled Compounds and Radiopharmaceuticals. XXVIII(10):1189-1199 (1990).
Wootton, et al., "Statistics of Local Complexity in Amino Acid Sequences and Sequence Databases", Comput. Chem. 17(2):149-63 (1993).

* cited by examiner

SEQUENCE LISTING

```
<160> NUMBER OF SEQ ID NOS: 45

<210> SEQ ID NO 1
<211> LENGTH: 189
<212> TYPE: PRT
<213> ORGANISM: Homo sapiens

<400> SEQUENCE: 1

Met Thr Glu Tyr Lys Leu Val Val Gly Ala Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 2
<211> LENGTH: 189
<212> TYPE: PRT
```

<213> ORGANISM: Homo sapiens

<400> SEQUENCE: 2

```
Met Thr Glu Tyr Lys Leu Val Val Val Gly Ala Asp Gly Val Gly Lys
1               5                   10                  15
Ser Ala Leu Thr Ile Gln Leu Ile Gln Asn His Phe Val Asp Glu Tyr
            20                  25                  30
Asp Pro Thr Ile Glu Asp Ser Tyr Arg Lys Gln Val Val Ile Asp Gly
        35                  40                  45
Glu Thr Cys Leu Leu Asp Ile Leu Asp Thr Ala Gly Gln Glu Glu Tyr
    50                  55                  60
Ser Ala Met Arg Asp Gln Tyr Met Arg Thr Gly Glu Gly Phe Leu Cys
65                  70                  75                  80
Val Phe Ala Ile Asn Asn Thr Lys Ser Phe Glu Asp Ile His His Tyr
                85                  90                  95
Arg Glu Gln Ile Lys Arg Val Lys Asp Ser Glu Asp Val Pro Met Val
            100                 105                 110
Leu Val Gly Asn Lys Cys Asp Leu Pro Ser Arg Thr Val Asp Thr Lys
        115                 120                 125
Gln Ala Gln Asp Leu Ala Arg Ser Tyr Gly Ile Pro Phe Ile Glu Thr
    130                 135                 140
Ser Ala Lys Thr Arg Gln Arg Val Glu Asp Ala Phe Tyr Thr Leu Val
145                 150                 155                 160
Arg Glu Ile Arg Gln Tyr Arg Leu Lys Lys Ile Ser Lys Glu Glu Lys
                165                 170                 175
Thr Pro Gly Cys Val Lys Ile Lys Lys Cys Ile Ile Met
            180                 185
```

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = guanidinophenylalanine
<222> LOCATION: (3)..(4)

<400> SEQUENCE: 3

Gln Gln Xaa Xaa
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = guanidinophenylalanine
<222> LOCATION: (4)..(4)

<400> SEQUENCE: 4

Leu Arg Gly Xaa
1

<210> SEQ ID NO 5
<211> LENGTH: 5
<212> TYPE: PRT
<213> ORGANISM: Artificial Sequence
<220> FEATURE:
<223> OTHER INFORMATION: Synthetic Peptide

```
<220> FEATURE:
<221> NAME/KEY: Xaa = guanidinophenylalanine
<222> LOCATION: (5)..(5)

<400> SEQUENCE: 5

Leu Arg Gly Asp Xaa
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = bromophenylalanine
<222> LOCATION: (4)..(4)

<400> SEQUENCE: 6

Leu Arg Gly Xaa
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = guanidinophenylalanine
<222> LOCATION: (3)..(4)

<400> SEQUENCE: 7

Leu Gln Xaa Xaa
1

<210> SEQ ID NO 8
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = guanidinophenylalanine
<222> LOCATION: (3)..(4)

<400> SEQUENCE: 8

Gln Arg Xaa Xaa
1

<210> SEQ ID NO 9
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = guanidinophenylalanine
<222> LOCATION: (4)..(4)

<400> SEQUENCE: 9

Gln Gln Gly Xaa
1

<210> SEQ ID NO 10
<211> LENGTH: 4
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: Xaa = guanidinophenylalanine
<222> LOCATION: (3)..(3)
<220> FEATURE:
<221> NAME/KEY: Xaa = bromophenylalanine
<222> LOCATION: (4)..(4)

<400> SEQUENCE: 10

Gln Gln Xaa Xaa
1

<210> SEQ ID NO 11
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = guanidinophenylalanine
<222> LOCATION: (4)..(4)

<400> SEQUENCE: 11

Gln Arg Gly Xaa
1

<210> SEQ ID NO 12
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = guanidinophenylalanine
<222> LOCATION: (4)..(4)

<400> SEQUENCE: 12

Leu Gln Gly Xaa
1

<210> SEQ ID NO 13
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = guanidinophenylalanine
<222> LOCATION: (3)..(4)

<400> SEQUENCE: 13

Leu Arg Xaa Xaa
1

<210> SEQ ID NO 14
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 14

Gln Asp Asn Tyr
1

<210> SEQ ID NO 15
<211> LENGTH: 5
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: Xaa = guanidinophenylalanine
<222> LOCATION: (5)..(5)

<400> SEQUENCE: 15

Gln Gln Gly Asp Xaa
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = guanidinophenylalanine
<222> LOCATION: (5)..(5)

<400> SEQUENCE: 16

Gln Arg Gly Asp Xaa
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = guanidinophenylalanine
<222> LOCATION: (5)..(5)

<400> SEQUENCE: 17

Leu Gln Gly Asp Xaa
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = guanidinophenylalanine
<222> LOCATION: (3)..(3)
<220> FEATURE:
<221> NAME/KEY: Xaa = guanidinophenylalanine
<222> LOCATION: (5)..(5)

<400> SEQUENCE: 18

Leu Arg Xaa Asp Xaa
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = bromophenylalanine
<222> LOCATION: (5)..(5)

<400> SEQUENCE: 19

Leu Arg Gly Asp Xaa
1               5
```

```
<210> SEQ ID NO 20
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = bromophenylalanine
<222> LOCATION: (4)..(4)

<400> SEQUENCE: 20

Gln Gln Gly Xaa
1

<210> SEQ ID NO 21
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = bromophenylalanine
<222> LOCATION: (4)..(4)

<400> SEQUENCE: 21

Gln Arg Gly Xaa
1

<210> SEQ ID NO 22
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = bromophenylalanine
<222> LOCATION: (4)..(4)

<400> SEQUENCE: 22

Leu Gln Gly Xaa
1

<210> SEQ ID NO 23
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = guanidinophenylalanine
<222> LOCATION: (3)..(3)
<220> FEATURE:
<221> NAME/KEY: Xaa = bromophenylalanine
<222> LOCATION: (4)..(4)

<400> SEQUENCE: 23

Leu Arg Xaa Xaa
1

<210> SEQ ID NO 24
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = guanidinophenylalanine
<222> LOCATION: (3)..(3)

<400> SEQUENCE: 24
```

```
Gln Asn Xaa Tyr
1

<210> SEQ ID NO 25
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 25

Asn Asp Glu Thr Tyr
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 26

Pro Ser Glu Glu Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 27

Ser Glu Glu Gly Gly
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 28

Glu Gly Thr Gly Thr
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 29

Tyr Glu Gln Gly Glu
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 30

Tyr Gly Glu Gln Glu
```

```
<210> SEQ ID NO 31
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 31

Leu Arg Gly Asp Arg
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 32

Gln Glu Lys Pro Pro
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 33

Glu Leu Thr Phe Gly
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 34

Val Arg Gly Asp Arg
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 35

Leu Arg Gly Pro Arg
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 36

Leu Arg Gly Glu Arg
1               5
```

```
<210> SEQ ID NO 37
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = homoarginine
<222> LOCATION: (2)..(2)

<400> SEQUENCE: 37

Leu Xaa Gly Asp Arg
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = homoarginine
<222> LOCATION: (5)..(5)

<400> SEQUENCE: 38

Leu Arg Gly Asp Xaa
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 39

His His His His His His
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (6)..(6)
<223> OTHER INFORMATION: C-terminal R residue can be deleted

<400> SEQUENCE: 40

Arg Arg Arg Arg Arg Arg
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = guanidinophenylalanine
<222> LOCATION: (2)..(2)

<400> SEQUENCE: 41

Leu Xaa Gly Asp Arg
1               5
```

```
<210> SEQ ID NO 42
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = guanidinophenylalanine
<222> LOCATION: (5)..(5)

<400> SEQUENCE: 42

Leu Arg Gly Ala Xaa
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 43

Leu Arg Gly Asn Arg
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 44

Leu Arg Gly Gln Arg
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 45

Leu Arg Gly Ala Arg
1               5
```

KRAS-SPECIFIC CAPTURE AGENTS, COMPOSITIONS, AND METHODS OF MAKING AND USING

CROSS-REFERENCE TO RELATED APPLICATIONS

This application claims benefit of U.S. Provisional Application No. 62/876,598, filed Jul. 19, 2019. Application No. 62/876,598, filed Jul. 19, 2019, is hereby incorporated herein by reference in its entirety.

REFERENCE TO SEQUENCE LISTING

The Sequence Listing submitted Oct. 16, 2020, as a text file named "INDI_107_ST25.txt," created on Oct. 9, 2020, and having a size of 12,279 bytes is hereby incorporated by reference pursuant to 37 C.F.R. § 1.52(e)(5).

FIELD OF THE INVENTION

The disclosed invention is generally in the field of cyclic peptides and specifically in the area of cyclic peptides that bind KRAS and methods of making and using such cyclic peptides.

BACKGROUND OF THE INVENTION

The KRAS oncogene is a member of the Ras family of GTPases that are involved in numerous cellular signaling processes. KRAS mutations are gain-of-function mutations that are present in up to 30% of all tumors, including as many as 90% of pancreatic cancers. Due to the clinical significance of this protein, many attempts have been made to develop Ras inhibitors, but such attempts have been mostly unsuccessful. This is largely due to the difficulty in outcompeting GTP for the KRAS binding pocket in cells, and the lack of known allosteric regulatory sites.

BRIEF SUMMARY OF THE INVENTION

Disclosed are compounds, compositions, and methods involving cyclic peptides that can bind to KRAS (G12D) oncogenic protein. For example, disclosed are cyclic peptides that selectively bind KRAS (G12D) oncogenic protein. In some forms, the cyclic peptide is represented by Formula I:

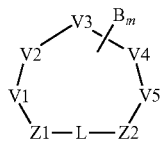

where:
Z1 and Z2 are each independently absent, aminoazidobutanoic acid (Az2), azidoornithine (OrnN3), L-azidolysine (Az4), or L-propargylglycine (Pra);
V1 is Q or L, V2 is Q or R, V3 is guanidinophenylalanine (Gnf) or G, V4 is absent or D, V5 is Gnf or bromophenylalanine (F—Br);
L is a linker; and
$B_m$ is an optional group, wherein m is 0 or 1.
In some forms, V1-V2-V3-V4-V5 is the sequence QQGnfGnf (SEQ ID NO:3), LRGGnf (SEQ ID NO:4), LRGDGnf (SEQ ID NO:5), LRGF-Br (SEQ ID NO:6), LQGnfGnf (SEQ ID NO:7), QRGnfGnf (SEQ ID NO:8), QQGGnf (SEQ ID NO:9), QQGnfF-Br (SEQ ID NO:10), QRGGnf (SEQ ID NO:11), LQGGnf (SEQ ID NO:12), LRGnfGnf (SEQ ID NO:13), QQGDGnf (SEQ ID NO:15), QRGDGnf (SEQ ID NO:16), LQGDGnf (SEQ ID NO:17), LRGnfDGnf (SEQ ID NO:18), LRGDF-Br (SEQ ID NO:19), QQGF-Br (SEQ ID NO:20), QRGF-Br (SEQ ID NO:21), LQGF-Br (SEQ ID NO:22), or LRGnfF-Br (SEQ ID NO:23).

In some forms, Z1 and Z2 are both absent. In some forms, when Z1 is Az2, OrnN3, Az4, or Pra, Z2 is absent and when Z2 is Az2, OrnN3, Az4, or Pra, Z2 is absent. In some forms, Z1 is absent and Z2 is Az2. In some forms, Z1 is Pra and Z2 is Az2. In some forms, Z1 is absent and Z2 is OrnN3. In some forms, Z1 is Pra and Z2 is OrnN3. In some forms, Z1 is absent and Z2 is Az4. In some forms, Z1 is Pra and Z2 is Az4. In some forms, Z1 is Az2 and Z2 is absent. In some forms, Z1 is Az2 and Z2 is Pra. In some forms, Z1 is OrnN3 and Z2 is absent. In some forms, Z1 is OrnN3 and Z2 is Pra. In some forms, Z1 is Az4 and Z2 is absent. In some forms, Z1 is Az4 and Z2 is Pra. In some forms, Z1 is not Pra if Z2 is OrnN3. In some forms, Z1 is not Pra if Z2 is Az4. In some forms, Z1 is not OrnN3 if Z2 is Pra. In some forms, Z1 is not Az4 if Z2 is Pra.

In some forms, L is 1,4-triazole or 1,5-triazole. In some forms, L is 1,4-substituted-1,2,3-triazole (Tz4) or a 1,5-substituted-1,2,3-triazole (Tz5). In some forms, L is 1,4-substituted-1,2,3-triazole residue (Tz4). In some forms, L is 1,5-substituted-1,2,3-triazole residue (Tz5).

In some forms, when m is 1, B is a spacer group, a detection tag, or a combination of a spacer group and a detection tag. In some forms, the spacer group is polyethylene glycol (PEG) or 6-aminohexanoic acid (Ahx). In some forms, the detection tag is an affinity tag, a fluorescent tag, or a fluorescently labeled affinity tag. In some forms, the detection tag is selected from the group consisting of biotin, streptavidin, poly-histidine, poly-arginine, FLAG, cyclodextrin, adamantane, copper-DOTA, biotin-PEG3, aminooxyacetate, $^{19}$FB, $^{18}$FB, FITC-PEG$_3$, $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C, $^{76}$Br, and combinations thereof. In some forms, the spacer group is PEG and the detection tag is biotin.

Also disclosed are methods of inhibiting KRAS (G12D) oncogenic protein in a cancer cell expressing KRAS (G12D) oncogenic protein. In some forms, the method comprises incubating the cancer cell with any one or more of the disclosed cyclic peptides. In some forms, the method comprises bringing into contact the cancer cell with any one or more of the disclosed cyclic peptides.

In some forms, the cancer cell is a pancreatic, colorectal, lung, biliary tract, or ovarian cancer cell. In some forms, the cancer cell is in a subject. In some forms, the incubation is accomplished by administering the composition to the subject. In some forms, the cancer cell and the cyclic peptide are brought into contact by administering the composition to the subject.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION OF THE INVENTION

Figure 1:
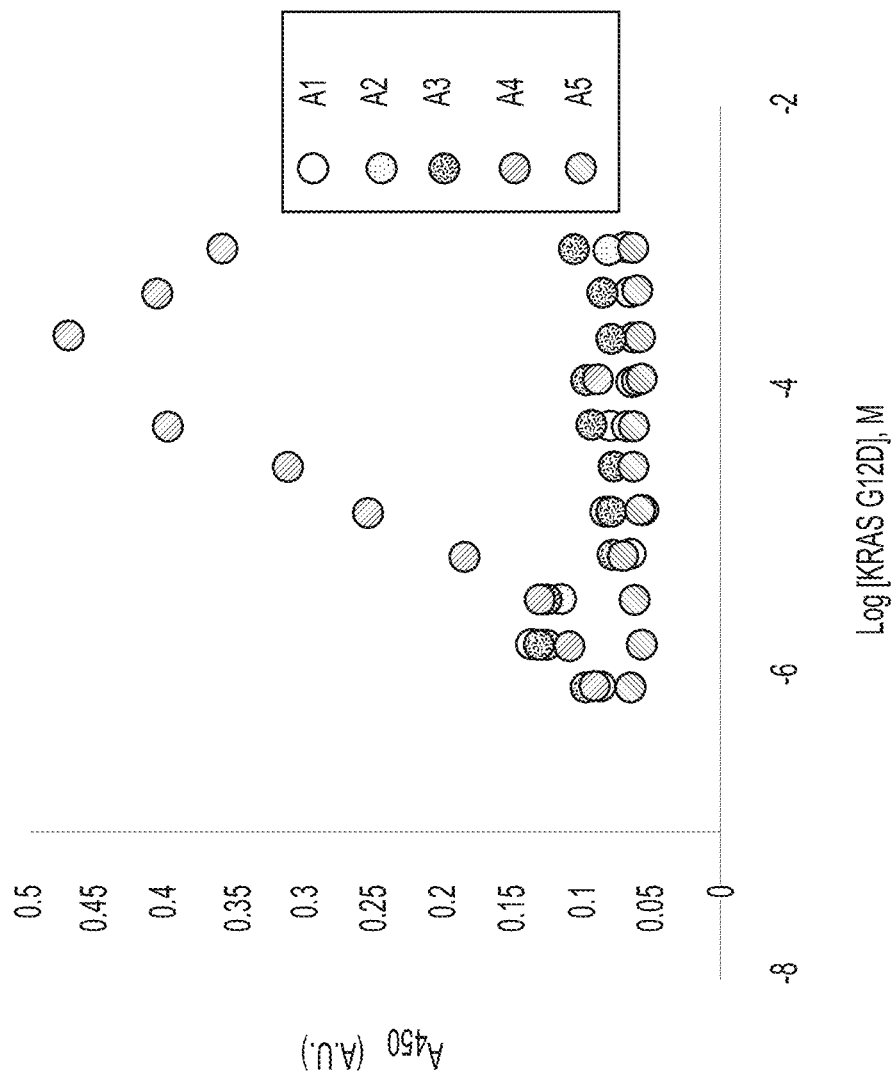
FIG. 1 is a graph of the amount of absorbance units (A.U.) in an ELISA assay measuring the binding to KRAS (G12D) in the presence of alanine-substituted cyclic peptide 7b10 (LRGDGnf; SEQ ID NO:5), in which alanine (A) was substituted in each position of the X variable region, giving cyclic peptides 7b10-A1 (A1) (red), 7b10-A2 (A2) (green), 7b10-A3 (A3)(purple), 7b10-A4 (A4)(blue), and 7b10-A5 (A5)(orange), where only 7b10-A4 maintained its binding affinity for KRAS (G12D). This shows that D at position 4 is not necessary for binding of the cyclic peptide.
Figure 2:
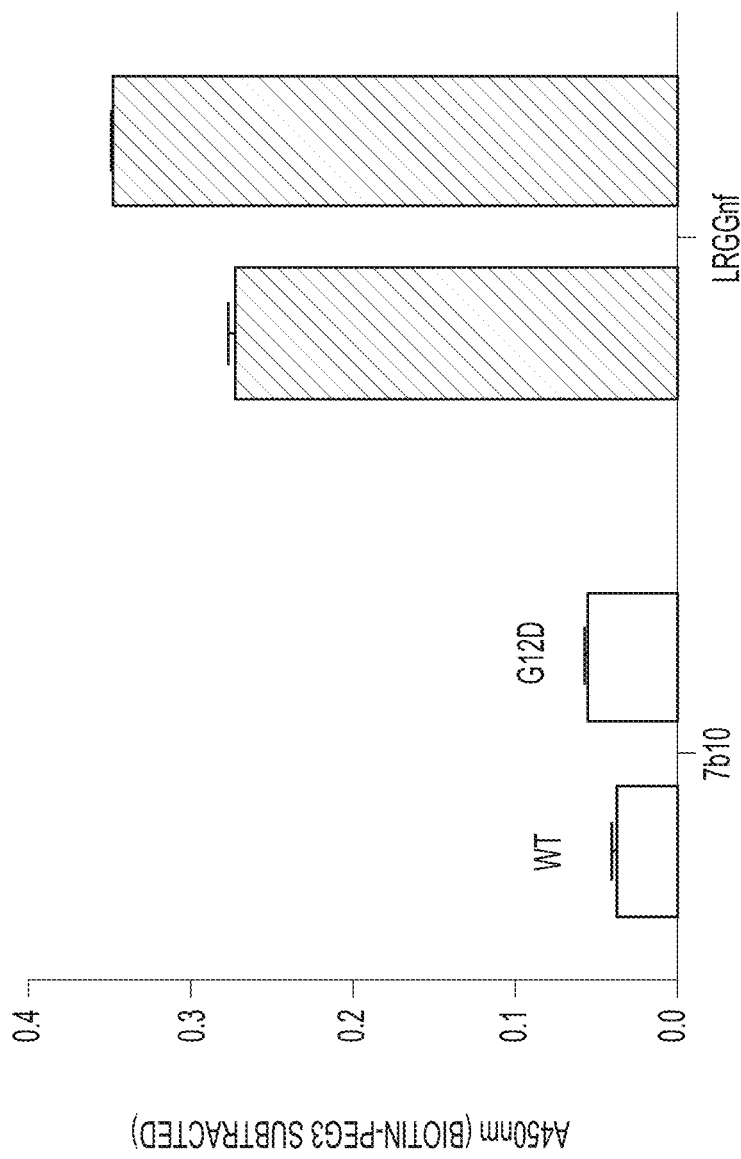
FIG. 2 is a graph of a single point ELISA assay comparing the binding (measured in absorbance units, A.U.) of cyclic peptide 7b10 (LRGDGnf; SEQ ID NO:5) and LRGGnf (SEQ ID NO:4) to KRAS (WT) and KRAS (G12D). LRGGnf (SEQ ID NO:4) shows 5 times greater binding compared to LRGDGnf (SEQ ID NO:5).
Figure 3:
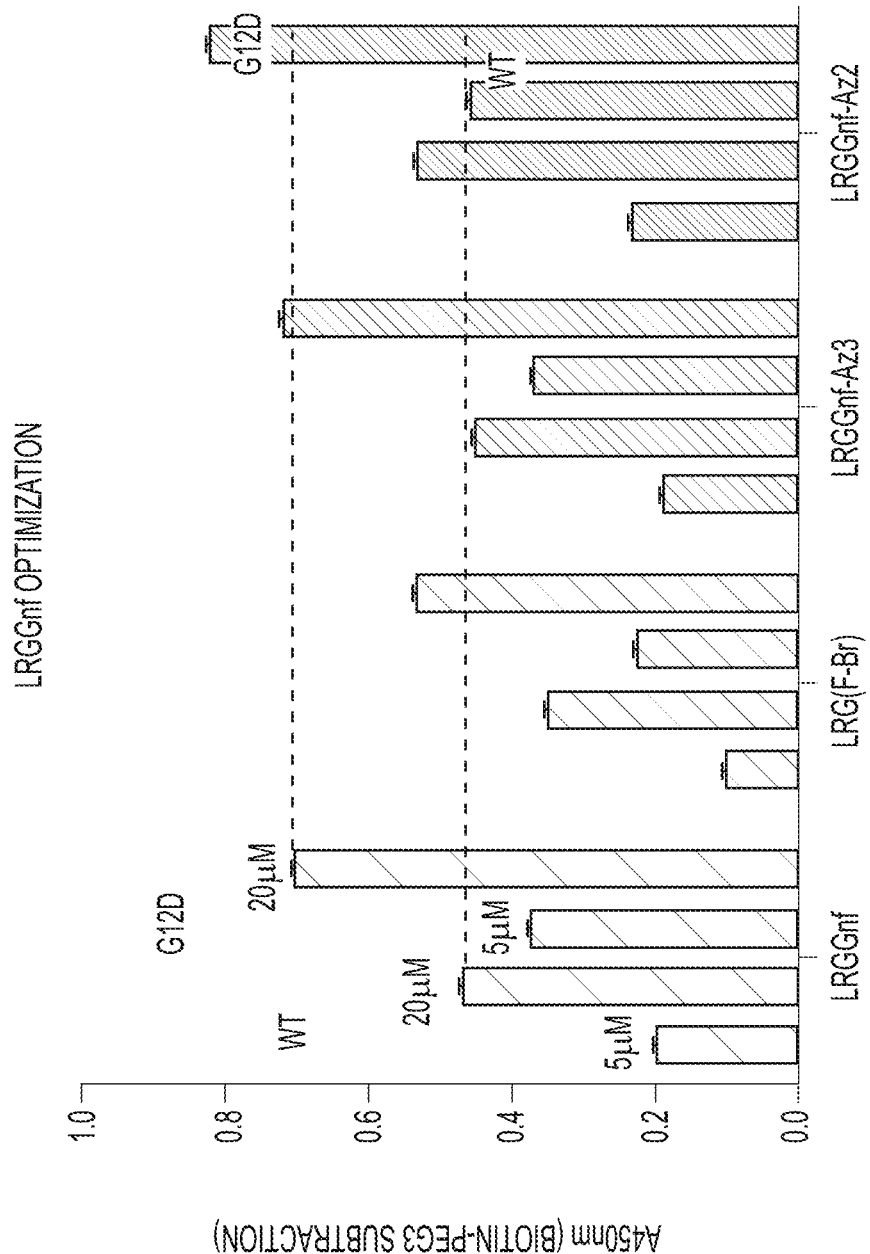
FIG. 3 is a graph of ELISA assays of four peptides (LRGGnf (SEQ ID NO:4), LRG (F—Br) (SEQ ID NO:6), LRGGnf-Az3 (SEQ ID NO:4), and LRGGnf-Az2 (SEQ ID NO:4)) at two different concentrations (5 μM and 20 μM) to KRAS (WT) and KRAS (G12D) comparing the binding (measured in absorbance units, A.U.). LRGGnf-Az3 (SEQ ID NO:4) is comparable to LRGGnf (SEQ ID NO:4) while LRGGnf-Az2 (SEQ ID NO:4) is slightly better and LRG (F—Br) (SEQ ID NO:6) is noticeable worse than LRGGnf (SEQ ID NO:4). All of the cyclic peptides show preferential binding to KRAS (G12D) over KRAS (WT).
Figure 4:
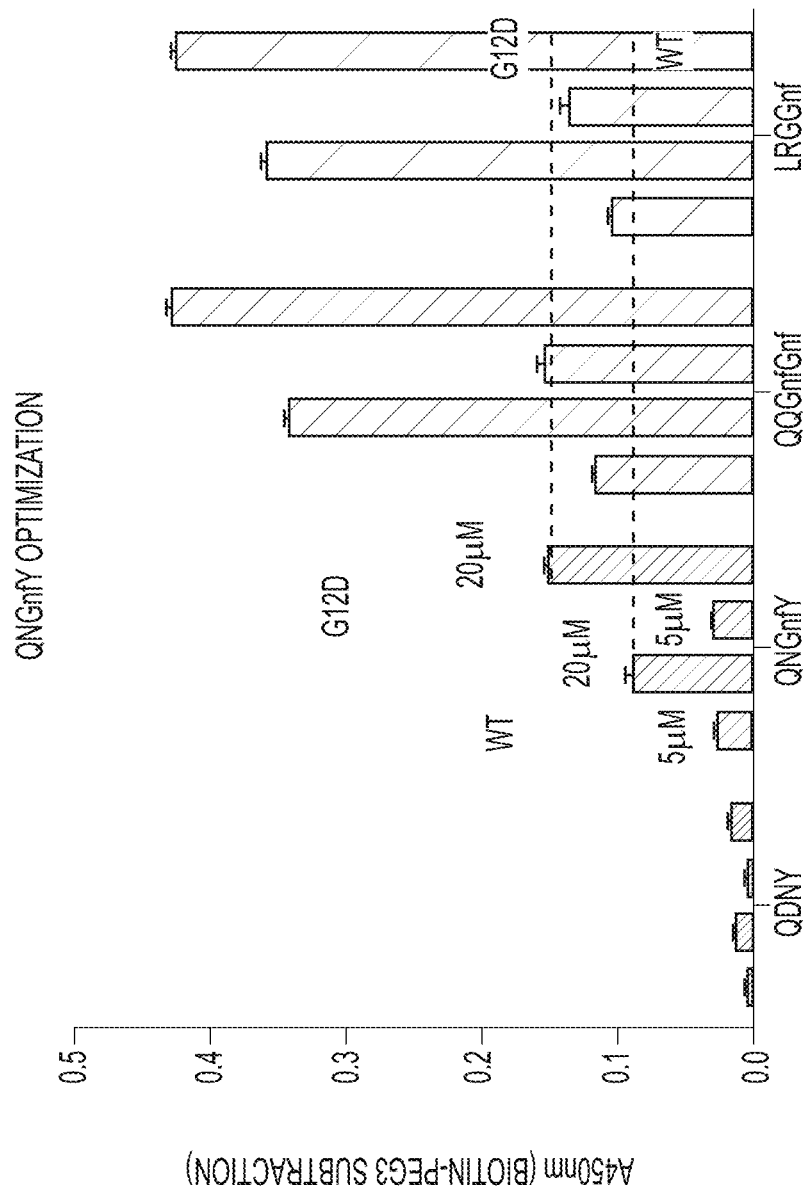
FIG. 4 is a graph of ELISA assays of four peptides (QDNY (SEQ ID NO:14), QNGnfY (SEQ ID NO:24), QQGnfGnf (SEQ ID NO:3), and LRGGnf (SEQ ID NO:4)) at two different concentrations (5 μM and 20 μM) to KRAS (WT) and KRAS (G12D) comparing the binding (measured in absorbance units, A.U.). QQGnfGnf (SEQ ID NO:3) is comparable to LRGGnf (SEQ ID NO:4) while QNGnfY (SEQ ID NO:24) is significantly worse and QDNY (SEQ ID NO:14) more so than LRGGnf (SEQ ID NO:4). All of the cyclic peptides show preferential binding to KRAS (G12D) over KRAS (WT).

The disclosed method and compositions may be understood more readily by reference to the following detailed description of particular embodiments and the Example included therein and to the Figures and their previous and following description.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Unless the context requires otherwise, throughout the present specification and claims, the word "comprise" and variations thereof, such as, "comprises" and "comprising" are to be construed in an open, inclusive sense—that is as "including, but not limited to."

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Disclosed are cyclic peptides, such as cyclic peptides of Formula 1, that selectively bind the most frequent KRAS mutation—the oncogenic KRAS protein having a glycine 12 to aspartic acid (G12D) mutation. The KRAS (G12D) mutant accounts for nearly half of all KRAS oncoproteins. Cyclic peptides as disclosed are capable of binding to the surface of KRAS (G12D), thus circumventing difficulties encountered with inhibitors requiring a binding pocket in KRAS.

Abbreviations for amino acids are used throughout this disclosure and follow the standard nomenclature known in the art. For example, as would be understood by those of skill in the art, Alanine is Ala or A; Arginine is Arg or R; Asparagine is Asn or N; Aspartic Acid is Asp or D; Cysteine is Cys or C; Glutamic acid is Glu or E; Glutamine is Gln or Q; Glycine is Gly or G; Histidine is His or H; Isoleucine is Ile or I; Leucine is Leu or L; Lysine is Lys or K; Methionine is Met or M; Phenylalanine is Phe or F; Proline is Pro or P; Serine is Ser or S; Theonine is Thr or T; Tryptophan is Trp or W; Tyrosine is Tyr or Y; and Valine is Val or V. Synthetic amino acids include L-propargylglycine (Fra), homoarginine (homoArg or homoR), guanidinophenylalanine (guanidinoF or Gnf), L-azidolysine (Az4), azidoornithine (OrnN3 or Az3), aminoazidobutanoic acid (Az2), or bromophenylalanine (F—Br).

A. Definitions

"Amino" refers to the —NH$_2$ radical.
"Cyano" refers to the —CN radical.
"Hydroxy" or "hydroxyl" refers to the —OH radical.
"Imino" refers to the =NH substituent.
"Nitro" refers to the —NO$_2$ radical.
"Oxo" refers to the =O substituent.
"Thioxo" refers to the =S substituent.
"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n propyl, 1 methylethyl (isopropyl), n-butyl, n-pentyl, 1,1 dimethylethyl (t-butyl), 3 methylhexyl, 2 methylhexyl, ethenyl, prop-1-enyl, but-1-enyl, pent-1-enyl, penta 1,4 dienyl, ethynyl, propynyl, butynyl, pentynyl, hexynyl, and the like. Unless stated otherwise specifically in the specification, an alkyl group can be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain can be optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group can be optionally substituted.

"Aminocarbonyl" refers to a radical of the formula —C(=O)NR$_a$R$_a$, where each R$_a$ is independently H, alkyl or a linker.

"α-amino carbonyl" refers to a radical of the formula —C(=O)CR$_b$(NR$_a$R$_a$), where each R$_a$ is independently H, alkyl or a linker and R$_b$ is H or alkyl. In some forms, an alpha amino carbonyl is part of a cyclic moiety (e.g., peptide) where the carbonyl is within the ring and the amino (NR$_a$R$_a$) is exocyclic. For example, in some forms, an alpha aminocarbonyl is useful for Edman degradation of cyclic peptides.

"α-amido carbonyl" refers to a radical of the formula —C(=O)CR$_b$(N(C=O)R$_a$R$_a$), where each R$_a$ is independently H, alkyl or a linker and R$_b$ is H or alkyl. In some forms, an alpha amido carbonyl is part of a cyclic moiety (e.g., peptide) where the carbonyl is within the ring and the amido (N(C=O)R$_a$R$_a$) is exocyclic.

"Alkylamino" refers to a radical of the formula —NHR$_a$ or —NR$_a$R$_a$ where each R$_a$ is, independently, an alkyl radical as defined above containing one to twelve carbon atoms. Unless stated otherwise specifically in the specification, an alkylamino group can be optionally substituted.

"Thioalkyl" refers to a radical of the formula —SR$_a$ where R$_a$ is an alkyl radical as defined above containing one to twelve carbon atoms. Unless stated otherwise specifically in the specification, a thioalkyl group can be optionally substituted.

"Aryl" refers to a hydrocarbon ring system radical comprising hydrogen, 6 to 18 carbon atoms and at least one aromatic ring. The aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. Unless stated otherwise specifically in the specification, an aralkyl group can be optionally substituted.

"Cycloalkyl" or "carbocyclic ring" refers to a stable non aromatic monocyclic or polycyclic hydrocarbon radical consisting solely of carbon and hydrogen atoms, which can include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7 dimethyl bicyclo[2.2.1]heptanyl, and the like. Unless otherwise stated specifically in the specification, a cycloalkyl group can be optionally substituted.

"Cycloalkylalkyl" refers to a radical of the formula —R$_b$R$_d$ where R$_b$ is an alkylene chain as defined above and R$_d$ is a cycloalkyl radical as defined above. Unless stated otherwise specifically in the specification, a cycloalkylalkyl group can be optionally substituted.

"Fused" refers to any ring structure described herein which is fused to an existing ring structure in the disclosed compounds. When the fused ring is a heterocyclyl ring or a heteroaryl ring, any carbon atom on the existing ring structure which becomes part of the fused heterocyclyl ring or the fused heteroaryl ring can be replaced with a nitrogen atom.

"Halo" or "halogen" refers to bromo, chloro, fluoro or iodo. "Haloalkyl" refers to an alkyl radical, as defined above, that is substituted by one or more halo radicals, as defined above, e.g., trifluoromethyl, difluoromethyl, trichloromethyl, 2,2,2 trifluoroethyl, 1,2 difluoroethyl, 3 bromo 2 fluoropropyl, 1,2 dibromoethyl, and the like. Unless stated otherwise specifically in the specification, a haloalkyl group can be optionally substituted.

"Heterocyclyl" or "heterocyclic ring" refers to a stable 3 to 18 membered non aromatic ring radical which consists of two to twelve carbon atoms and from one to six heteroatoms selected from the group consisting of nitrogen, oxygen and sulfur. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2 oxopiperazinyl, 2 oxopiperidinyl, 2 oxopyrrolidinyl, oxazolidinyl, piperidinyl, piperazinyl, 4 piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1 oxo thiomorpholinyl, and 1,1 dioxo thiomorpholinyl. Unless stated otherwise specifically in the specification, a heterocyclyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, an N-heterocyclyl group can be optionally substituted.

"Heterocyclylalkyl" refers to a radical of the formula —RbRe where Rb is an alkylene chain as defined above and Re is a heterocyclyl radical as defined above, and if the heterocyclyl is a nitrogen containing heterocyclyl, the heterocyclyl can be attached to the alkyl radical at the nitrogen atom. Unless stated otherwise specifically in the specification, a heterocyclylalkyl group can be optionally substituted.

"Heteroaryl" refers to a 5 to 14 membered ring system radical comprising hydrogen atoms, one to thirteen carbon atoms, one to six heteroatoms selected from the group consisting of nitrogen, oxygen and sulfur, and at least one aromatic ring. Generally, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4 benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2 a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2 oxoazepinyl, oxazolyl, oxiranyl, 1-oxidopyridinyl, 1 oxidopyrimidinyl, 1-oxidopyrazinyl, 1-oxidopyridazinyl, 1 phenyl 1H pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group can be optionally substituted.

The term "substituted" used herein means any of the above groups (e.g., alkyl, alkylene, alkoxy, alkylamino, aminocarbonyl, α-aminocarbonyl, α-amidocarbonyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, $OC(=O)$ $NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

"Mammal" includes humans and both domestic animals such as laboratory animals and household pets (e.g., cats, dogs, swine, cattle, sheep, goats, horses, rabbits), and non-domestic animals such as wildlife and the like. "Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

The compounds (e.g., cyclic peptides), or their pharmaceutically acceptable salts can contain one or more asymmetric centers and can thus give rise to enantiomers, diastereomers, and other stereoisomeric forms that can be defined, in terms of absolute stereochemistry, as (R) or (S) or, as (D) or (L) for amino acids. All such possible isomers, as well as their racemic and optically pure forms, can be used with the disclosed cyclic peptides. Optically active (+) and (−), (R) and (S), or (D) and (L) isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. (D)-amino acids (also referred to as D-amino acids) are referred to herein in lower case letters (e.g. D-valine is referred to as "v"), while (L)-amino acids (also referred to herein as L-amino acids) are referred to in upper case letters (e.g. L-valine or valine is referred to as "V"). Glycine is non-chiral and is referred to as "G."

A "stereoisomer" refers to a compound made up of the same atoms bonded by the same bonds but having different three-dimensional structures, which are not interchangeable. Various stereoisomers and mixtures thereof are contemplated and includes "enantiomers," which refers to two stereoisomers whose molecules are nonsuperimposeable mirror images of one another.

A "tautomer" refers to a proton shift from one atom of a molecule to another atom of the same molecule. Tautomers of any said compounds are specifically contemplated.

Often crystallizations produce a solvate of the compound. As used herein, the term "solvate" refers to an aggregate that comprises one or more molecules of a compound with one or more molecules of solvent. The solvent can be water, in which case the solvate can be a hydrate. Alternatively, the solvent can be an organic solvent. Thus, the compounds can exist as a hydrate, including a monohydrate, dihydrate, hemihydrate, sesquihydrate, trihydrate, tetrahydrate and the like, as well as the corresponding solvated forms. The compounds can be true solvates, while in other cases, the compounds can merely retain adventitious water or be a mixture of water plus some adventitious solvent.

The term "capture agent" as used herein refers to a composition that comprises two or more target-binding moieties (such as the disclosed cyclic peptides) and which specifically binds to a target protein via those target-binding moieties. Each target-binding moiety exhibits binding affinity for the target protein, either individually or in combination with other target-binding moieties. In some forms, each target-binding moiety binds to the target protein via one or more non-covalent interactions, including for example hydrogen bonds, hydrophobic interactions, and van der Waals interactions. A capture agent can comprise one or more organic molecules, including for example polypeptides, peptides, polynucleotides, and other non-polymeric molecules. In some aspects a capture agent is a protein catalyzed capture agent (PCC).

The term "epitope" as used herein refers to a distinct molecular surface of a protein (e.g., KRAS (G12D) or KRAS (WT)). Typically, the epitope is a polypeptide and it can act on its own as a finite sequence of 10-40 amino acids.

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, O-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid Amino acids can be referred to herein by either their commonly known three letter symbols or by the one-letter symbols recommended by the IUPAC-IUB Biochemical Nomenclature Commission.

The term "non-natural amino acid" as used herein refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. The non-natural amino acid can be a close analog of one of the twenty natural amino acids, or it can introduce a completely new functionality and chemistry, as long as the hydrophobicity of the non-natural amino acid is either equivalent to or greater than that of the natural amino acid. The non-natural amino acid can either replace an existing amino acid in a protein (substitution), or be an addition to the wild type sequence (insertion). The incorporation of non-natural amino acids can be accomplished by known chemical methods including solid-phase peptide synthesis or native chemical ligation, or by biological methods.

The terms "specific binding," "selective binding," "selectively binds," or "specifically binds" as used herein refer to cyclic peptide binding to an epitope on a predetermined antigen. Typically, the cyclic peptide binds with an affinity ($K_D$) of approximately less than $10^{-7}$ M, such as approximately less than $10^{-8}$ M, $10^{-9}$ M or $10^{-10}$ M or even lower.

The term "$K_D$" as used herein refers to the dissociation equilibrium constant of a particular cyclic peptide-antigen interaction. Typically, the cyclic peptides bind to KRAS with a dissociation equilibrium constant ($K_D$) of less than approximately $10^{-6}$ M, $10^{-7}$ M, such as less than approximately $10^{-8}$ M, $10^{-9}$ M or $10^{-10}$ M or even lower, for example, as determined using surface plasmon resonance (SPR) technology in a Biacore instrument using the antigen as the ligand and the cyclic peptide as the analyte, and binds to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the cyclic peptide, so that when the $K_D$ of the cyclic peptide is very low (that is, the cyclic peptide is highly specific), then the amount with which the affinity for the antigen is lower than the affinity for a non-specific antigen can be at least 10,000 fold.

The term "$k_d$" (sec$^{-1}$) as used herein refers to the dissociation rate constant of a particular cyclic peptide-antigen interaction. Said value is also referred to as the $k_{off}$ value.

The term "$k_a$" (M$^{-1}$×sec$^{-1}$) as used herein refers to the association rate constant of a particular cyclic peptide-antigen interaction.

The term "$K_D$" (M) as used herein refers to the dissociation equilibrium constant of a particular cyclic peptide-antigen interaction.

The term "$K_A$" (M$^{-1}$) as used herein refers to the association equilibrium constant of a particular cyclic peptide-antigen interaction and is obtained by dividing the $k_a$ by the $k_d$.

A "pharmaceutical composition" refers to a formulation of a compound and a medium generally accepted in the art for the delivery of the biologically active compound to mammals, e.g., humans. Such a medium includes all pharmaceutically acceptable carriers, diluents or excipients therefor.

The term "condition" as used herein refers generally to a disease, event, or a change in health status. A change in health status may be associated with a particular disease or event, in which case the change may occur simultaneously with or in advance of the disease or event. In those cases where the change in health status occurs in advance of a disease or event, the change in health status can serve as a predictor of the disease or event. For example, a change in health status can be an alteration in the expression level of a particular gene associated with a disease or event. Alternatively, a change in health status may not be associated with a particular disease or event.

The terms "treat," "treating," or "treatment" as used herein generally refer to preventing a condition or event, slowing the onset or rate of development of a condition or delaying the occurrence of an event, reducing the risk of developing a condition or experiencing an event, preventing or delaying the development of symptoms associated with a condition or event, reducing or ending symptoms associated with a condition or event, generating a complete or partial regression of a condition, lessening the severity of a condition or event, or some combination thereof.

An "effective amount" or "therapeutically effective amount" as used herein refers to an amount effective, at dosages and for periods of time necessary, to achieve a desired therapeutic result. A therapeutically effective amount of a disclosed cyclic peptide can vary according to factors such as the disease state, age, sex, and weight of the individual, and the ability of the cyclic peptide to elicit a desired response in the individual.

The term "stable" as used herein with regard to a cyclic peptide protein catalyzed cyclic peptide or pharmaceutical formulation thereof refers to the agent or formulation retaining structural and functional integrity for a sufficient period of time to be utilized in the methods described herein.

The term "synthetic" as used herein with regard to a protein catalyzed cyclic peptide or cyclic peptide refers to the cyclic peptide has been generated by chemical rather than biological means.

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which can be homopolymeric tracts, short-period repeats, or regions enriched in one or more amino acids. Such low-complexity regions can be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity can be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantially identical" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

In some forms, the term "KRAS (WT)" as used herein refers to human KRAS (WT). In some forms, KRAS (WT) comprises the following amino acid sequence or an amino acid sequence substantially identical to it.

```
                                        (SEQ ID NO: 1)
MTEYKLVVVG AGGVGKSALT IQLIQNHFVD EYDPTIEDSY

RKQVVIDGET CLLDILDTAG QEEYSAMRDQ YMRTGEGFLC

VFAINNTKSF EDIHHYREQI KRVKDSEDVP MVLVGNKCDL

PSRTVDTKQA QDLARSYGIP FIETSAKTRQ RVEDAFYTLV

REIRQYRLKK ISKEEKTPGC VKIKKCIIM
```

In some forms, the term "KRAS (G12D)" as used herein refers to human KRAS (G12D). In some forms, KRAS (G12D) comprises the following amino acid sequence or an amino acid sequence substantially identical to it.

```
                                        (SEQ ID NO: 2)
MTEYKLVVVG ADGVGKSALT IQLIQNHFVD EYDPTIEDSY

RKQVVIDGET CLLDILDTAG QEEYSAMRDQ YMRTGEGFLC

VFAINNTKSF EDIHHYREQI KRVKDSEDVP MVLVGNKCDL

PSRTVDTKQA QDLARSYGIP FIETSAKTRQ RVEDAFYTLV

REIRQYRLKK ISKEEKTPGC VKIKKCIIM
```

B. Cyclic Peptides

Disclosed are cyclic peptides that selectively bind KRAS (G12D) oncogenic protein. In some forms, the cyclic peptide is represented by Formula I:

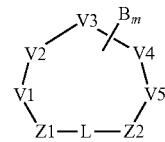

In some forms of cyclic peptides of Formula 1, Z1 is absent or a non-naturally occurring amino acid at the amino (N)-terminus, Z2 is absent or a non-naturally occurring amino acid at the carboxy (C)-terminus, and V1-V5 is a 4- or 5-amino acid variable region. The 4- or 5-amino acid variable region can also be represented as V1-V2-V3-V4-V5. Generally, for the 4-amino acid variable region, V4 is absent.

In some forms, Z1 and Z2 are not the same and are linked by a triazole group. In some form, Z1 and/or Z2 are absent and the ends are linked by a triazole group (as L). Z1 and Z2 can each independently be absent or independently represent a non-naturally occurring amino acid selected from L-propargylglycine (Pra), aminoazidobutanoic acid (Az2), azidoornithine (OrnN3), or L-azidolysine (Az4). In some forms, Z1 and Z2 are each independently absent, aminoazidobutanoic acid (Az2), azidoornithine (OrnN3), L-azidolysine (Az4), or L-propargylglycine (Pra). In some forms, Z1 and Z2 are both absent. In some forms, when Z1 is Az2, OrnN3, Az4, or Pra, Z2 is absent and when Z2 is Az2, OrnN3, Az4, or Pra, Z2 is absent. In some forms, Z1 is absent and Z2 is Az2. In some forms, Z1 is Pra and Z2 is Az2. In some forms, Z1 is absent and Z2 is OrnN3. In some forms, Z1 is Pra and Z2 is OrnN3. In some forms, Z1 is absent and Z2 is Az4. In some forms, Z1 is Pra and Z2 is Az4. In some forms, Z1 is Az2 and Z2 is absent. In some forms, Z1 is Az2 and Z2 is Pra. In some forms, Z1 is OrnN3 and Z2 is absent. In some forms, Z1 is OrnN3 and Z2 is Pra. In some forms, Z1 is Az4 and Z2 is absent. In some forms, Z1 is Az4 and Z2 is Pra. In some forms, Z1 is not Pra if Z2 is OrnN3. In some forms, Z1 is not Pra if Z2 is Az4. In some forms, Z1 is not OrnN3 if Z2 is Pra. In some forms, Z1 is not Az4 if Z2 is Pra.

L is a linker. In some forms, L links Z1 and Z2. In some forms, L links V1 and Z2. In some forms, L links Z1 and V5. In some forms, L is 1,4-triazole or 1,5-triazole. In some forms, L is 1,4-triazole or 1,5-triazole. In some forms, L is 1,4-substituted-1,2,3-triazole (Tz4) or a 1,5-substituted-1,2,3-triazole (Tz5). In some forms, L is 1,4-substituted-1,2,3-triazole residue (Tz4). In some forms, L is 1,5-substituted-1,2,3-triazole residue (Tz5).

In some forms, V1 is Q or L, V2 is Q or R, V3 is guanidinophenylalanine (Gnf) or G, V4 is absent or D, V5 is Gnf or bromophenylalanine (F—Br). In some forms, V1-V5 is a five amino acid region having an amino acid sequence selected from QQGnfGnf (SEQ ID NO:3), LRGGnf (SEQ ID NO:4), LRGDGnf (SEQ ID NO:5), LRGF-Br (SEQ ID NO:6), LQGnfGnf (SEQ ID NO:7), QRGnfGnf (SEQ ID NO:8), QQGGnf (SEQ ID NO:9), QQGnfF-Br (SEQ ID NO:10), QRGGnf (SEQ ID NO:11), LQGGnf (SEQ ID NO:12), LRGnfGnf (SEQ ID NO:13), QQGDGnf (SEQ ID NO:15), QRGDGnf (SEQ ID NO:16), LQGDGnf (SEQ ID NO:17), LRGnfDGnf (SEQ ID NO:18), LRGDF-Br (SEQ ID NO:19), QQGF-Br (SEQ ID NO:20), QRGF-Br (SEQ ID NO:21), LQGF-Br (SEQ ID NO:22), or LRGnfF-Br (SEQ ID NO:23).

$B_m$ is a an optional group, wherein m is 0 or 1. In some forms, when m is 1, B is a spacer group, a detection tag, or a combination of a spacer group and a detection tag. In some forms, the spacer group is polyethylene glycol (PEG) or 6-aminohexanoic acid (Ahx). In some forms, the detection tag is an affinity tag, a fluorescent tag, or a fluorescently labeled affinity tag. In some forms, the detection tag is selected from the group consisting of biotin, streptavidin, poly-histidine, poly-arginine, FLAG, cyclodextrin, adamantane, copper-DOTA, biotin-PEG3, aminooxyacetate, $^{19}$FB, $^{18}$FB, FITC-PEG$_3$, $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C, $^{76}$Br, and combinations thereof. In some forms, the spacer group is PEG and the detection tag is biotin.

In some forms, the cyclic peptide of Formula 1 can include $B_m$ representing an optional group, where m is 0 or 1. In some forms, B can be a spacer group and/or a detection tag. In some forms, when m is 1, B can be a spacer group, a detection tag, or a conjugate of both a spacer group and a detection tag. In some forms, B can be conjugated to any group of the cyclic peptide. In some forms, B can be conjugated to the C-terminus of Z2. For example, B can be conjugated to the C-terminus of Az4.

In some forms, non-limiting examples of a spacer group include polyethylene glycol (PEG)n or 6-aminohexanoic acid (Ahx). As known to those of skill in the art, the number of PEG units (n) (or ethylene glycol repeats) determines the length of the spacer group. For example, 2 PEG units provide a spacer length of 18 angstroms. In some forms, spacer group includes 2 to 24 PEG units, 2 to 20 PEG units, 2 to 15 PEG units, 2 to 10 PEG units, 2 to 5 PEG units, 2 to 4 PEG units, or 2 to 3 PEG units.

Examples of the disclosed cyclic peptides can have structures shown below.

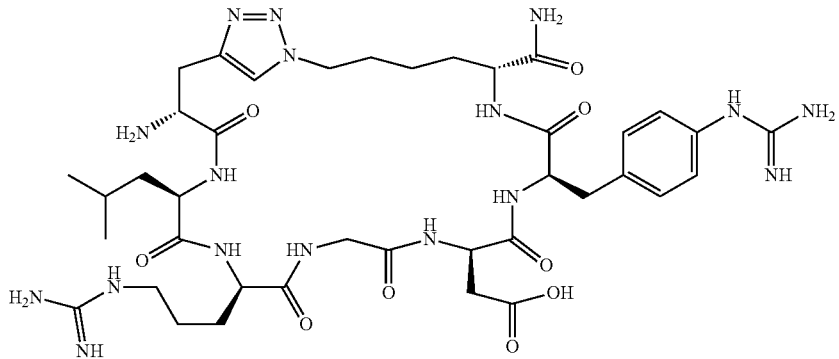

LRGDGnf (SEQ ID NO:5) (7b10)

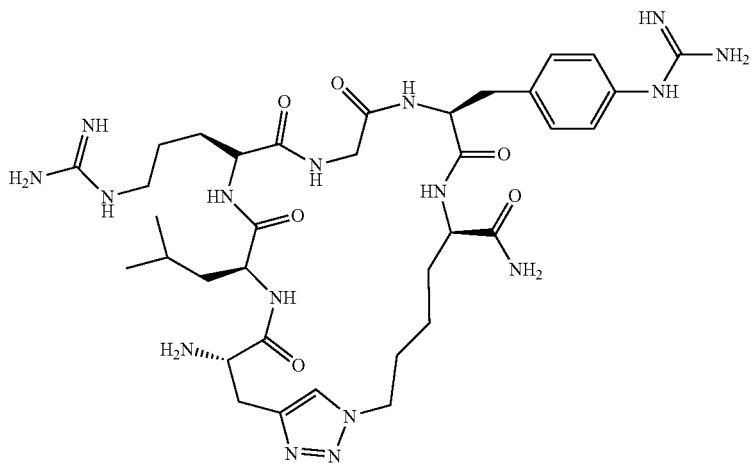

LRGDGnf-Tz4 (SEQ ID NO:5)

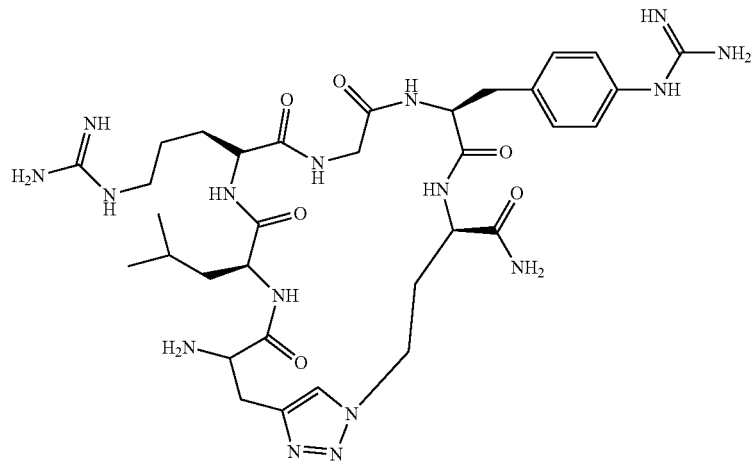

LRGDGnf-Tz2 (SEQ ID NO:5)

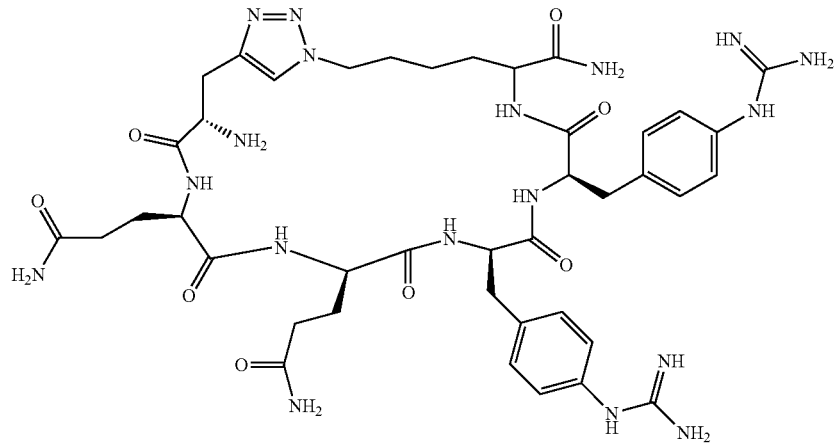

QQGnfGnf-Tz4 (SEQ ID NO:3)

The EC50 of LRGGnf-Tz2 (SEQ ID NO:4) 0.9 μM for KRAS (WT) and 0.6 μM for KRAS (G12D). The EC50 of QQGnfGnf-Tz4 (SEQ ID NO:3) 3 μM for KRAS (WT) and 1 μM for KRAS (G12D).

As used herein, "tag," "detection tag," and like terms refer to a covalently linked chemical moiety that can be selectively bound and isolated. In some forms, "tag" refers to an "affinity tag" in which the chemical moiety has a specific binding partner. Non-limiting examples of affinity tags include biotin, streptavidin, poly-histidine (6-HIS) (SEQ ID NO: 39), poly-arginine (5-6 R) (SEQ ID NO: 40), FLAG, cyclodextrin, adamantane, and combinations thereof. Affinity tags for labeling peptides are described, for example in K. Terpe, 2003, Appl. Microbiol. Biotechnol, 2003, 60:523-533, the entire contents of which are incorporated herein by reference. In some forms, the detection tag can be a fluorescent dye or can be a fluorescent dye conjugated to an affinity tag.

The cyclic peptides can be prepared by procedures known to those of skill in the art. For example, the cyclic peptides can be prepared using standard solid-phase peptide synthesis (SPPS) techniques as described for example, in Das et al. 2015, Angew. Chem. Int. Ed., 54: 1329-13224, the entire contents of which are incorporated herein by reference. Methods for synthesizing and cyclizing the peptides using azide/alkyne chemistry are described in more detail in the examples.

C. Therapeutic Applications

Figure 5:
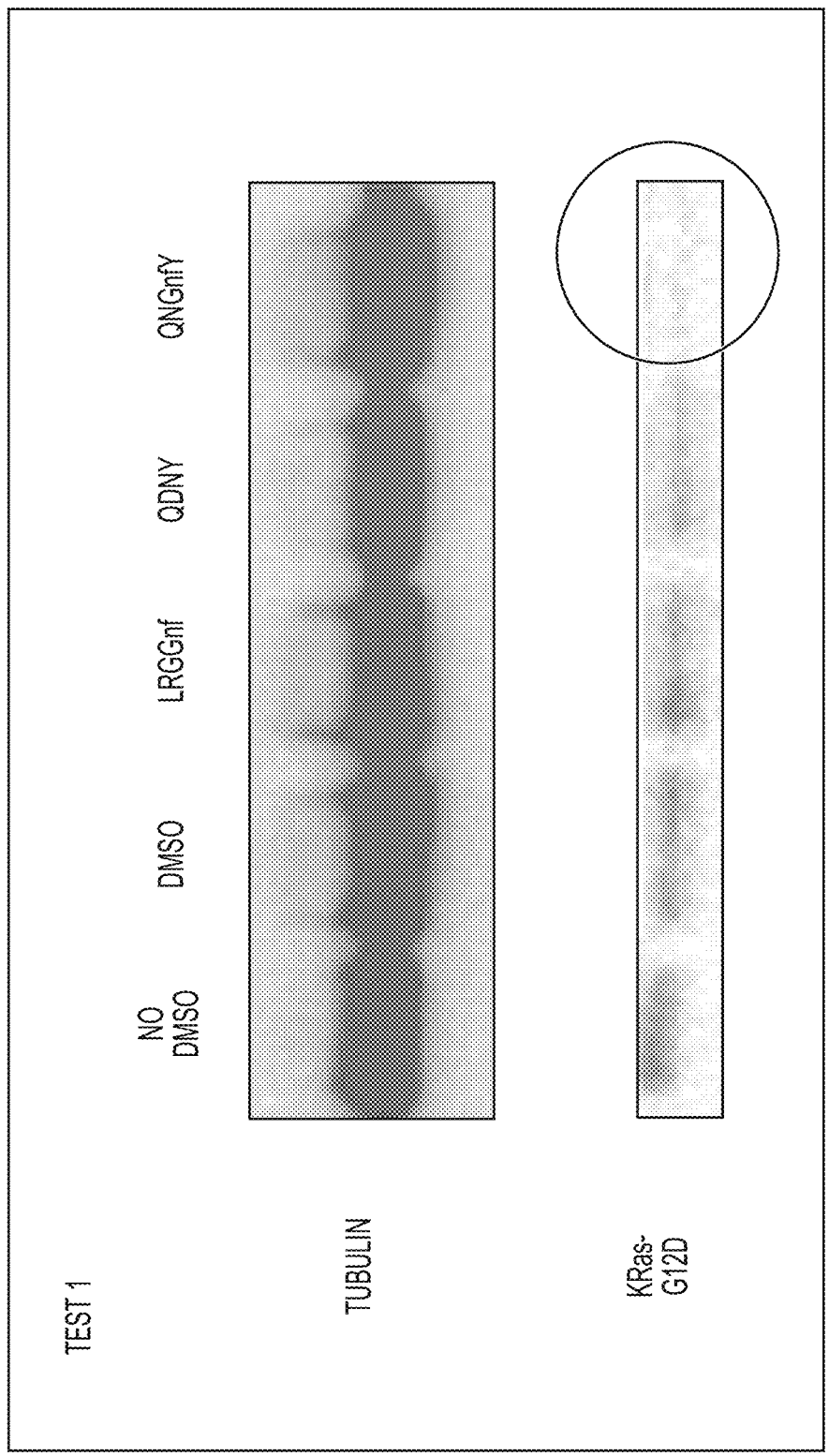
FIG. 5 is a Western blot analysis of KRAS (G12D) protein in Panc 08.13 cancer cells (homozygous for KRAS (G12D)) after treatment with no DMSO (control), DMSO (control), LRGGnf (SEQ ID NO:4), QDNY (SEQ ID NO:14), and QNGnfY (SEQ ID NO:24), as indicated, in which the cells treated with QNGnfY (SEQ ID NO:24) (and to a lesser extent, QDNY (SEQ ID NO:14)) show depletion of Ras protein.

The disclosed cyclic peptides can be used, for example, in methods for inhibiting the KRAS (G12D) oncoprotein. Such methods can include treating cancer cells having the KRAS (G12D) mutation. As shown in FIG. 5, cyclic peptide QNGnfY (SEQ ID NO:24) is capable of decreasing or depleting levels of KRAS (G12D) in pancreatic cancer cells as shown by Western blot analysis of a pancreatic cell lysate after the cells were incubated with the peptide. In some forms, a cyclic peptide of Formula I can be used to inhibit KRAS (G12D) expressed in any cancer cell. For example, the KRAS (G12D) oncoprotein has been identified in pancreatic, colorectal, lung, biliary tract, and ovarian cancer cells.

Provided herein are methods of using the KRAS (G12D) cyclic peptides disclosed herein to inhibit, identify, detect, and/or quantify KRAS (G12D) in a biological sample or a subject. In certain forms, these methods utilize an immunoassay, with the cyclic peptide replacing an antibody or its equivalent. In certain forms, the immunoassay can be a Western blot, pull-down assay, dot blot, or ELISA.

A biological sample for use in the methods provided herein can be selected from the group consisting of organs, tissue, bodily fluids, and cells. Where the biological sample is a bodily fluid, the fluid can be selected from the group consisting of blood, serum, plasma, urine, sputum, saliva, stool, spinal fluid, cerebral spinal fluid, lymph fluid, skin secretions, respiratory secretions, intestinal secretions, genitourinary tract secretions, tears, and milk. The organs include, e.g., the adrenal glands, bladder, bones, brain, breasts, cervix, esophagus, eyes, gall bladder, genitals, heart, kidneys, large intestine, liver, lungs, lymph nodes, ovaries, pancreas, pituitary gland, prostate, salivary glands, skeletal muscles, skin, small intestine, spinal cord, spleen, stomach, thymus gland, trachea, thyroid, testes, ureters, and urethra. Tissues include, e.g., epithelial, connective, nervous, and muscle tissues.

Provided herein are methods of using the KRAS (G12D) cyclic peptides disclosed herein to diagnose and/or classify (e.g., stage) a condition associated with KRAS (G12D) expression. In some forms, the methods comprise (a) obtaining a biological sample from a subject; (b) measuring the presence or absence of KRAS (G12D) in the sample with the KRAS (G12D) cyclic peptide; (c) comparing the levels of KRAS (G12D) to a predetermined control range for KRAS (G12D); and (d) diagnosing a condition associated with KRAS (G12D) expression based on KRAS (G12D) levels in the biological sample and the predetermined control.

In some forms, the KRAS (G12D) cyclic peptide is administered alone without delivering a radiopharmaceutical or another active agent.

In some forms, the cyclic peptides utilized in treatments. A therapeutic agent can be conjugated to one or more KRAS (G12D) cyclic peptides and administered to a patient.

Therapeutic agents and the KRAS (G12D) cyclic peptides disclosed herein can be linked or fused in known ways, optionally using the same type of linkers discussed elsewhere herein. Preferred linkers are substituted or unsubstituted alkyl chains, amino acid chains, polyethylene glycol chains, and other simple polymeric linkers known in the art.

The disclosed compositions and methods can be further understood through the following numbered paragraphs.

1. A cyclic peptide that selectively binds KRAS (G12D) oncogenic protein, wherein the cyclic peptide is represented by Formula I:

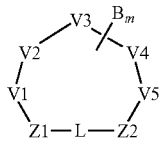

wherein:

Z1 and Z2 are each independently absent, aminoazidobutanoic acid (Az2), azidoornithine (OrnN3), L-azidolysine (Az4), or L-propargylglycine (Pra);

V1 is Q or L, V2 is Q or R, V3 is guanidinophenylalanine (Gnf) or G, V4 is absent or D, V5 is Gnf or bromophenylalanine (F—Br);

L is a linker; and $B_m$ is a an optional group, wherein m is 0 or 1.

2. The cyclic peptide of paragraph 1, wherein V1-V2-V3-V4-V5 is the sequence QQGnfGnf (SEQ ID NO:3), LRGGnf (SEQ ID NO:4), LRGDGnf (SEQ ID NO:5), LRGF-Br (SEQ ID NO:6), LQGnfGnf (SEQ ID NO:7), QRGnfGnf (SEQ ID NO:8), QQGGnf (SEQ ID NO:9), QQGnfF-Br (SEQ ID NO:10), QRGGnf (SEQ ID NO:11), LQGGnf (SEQ ID NO:12), LRGnfGnf (SEQ ID NO:13), QQGDGnf (SEQ ID NO:15), QRGDGnf (SEQ ID NO:16), LQGDGnf (SEQ ID NO:17), LRGnfDGnf (SEQ ID NO:18), LRGDF-Br (SEQ ID NO:19), QQGF-Br (SEQ ID NO:20), QRGF-Br (SEQ ID NO:21), LQGF-Br (SEQ ID NO:22), or LRGnfF-Br (SEQ ID NO:23).

3. The cyclic peptide of paragraph 1 or 2, wherein Z1 and Z2 are both absent.

4. The cyclic peptide of paragraph 1 or 2, wherein when Z1 is Az2, OrnN3, Az4, or Pra, Z2 is absent and when Z2 is Az2, OrnN3, Az4, or Pra, Z2 is absent.

5. The cyclic peptide of paragraph 1, 2, or 4, wherein Z1 is absent and Z2 is Az2.

6. The cyclic peptide of paragraph 1, 2, or 4, wherein Z1 is Pra and Z2 is Az2.

7. The cyclic peptide of paragraph 1, 2, or 4, wherein Z1 is absent and Z2 is OrnN3.

8. The cyclic peptide of paragraph 1, 2, or 4, wherein Z1 is Pra and Z2 is OrnN3.

9. The cyclic peptide of paragraph 1, 2, or 4, wherein Z1 is absent and Z2 is Az4.

10. The cyclic peptide of paragraph 1, 2, or 4, wherein Z1 is Pra and Z2 is Az4.

11. The cyclic peptide of paragraph 1, 2, or 4, wherein Z1 is Az2 and Z2 is absent.

12. The cyclic peptide of paragraph 1, 2, or 4, wherein Z1 is Az2 and Z2 is Pra.

13. The cyclic peptide of paragraph 1, 2, or 4, wherein Z1 is OrnN3 and Z2 is absent.

14. The cyclic peptide of paragraph 1, 2, or 4, wherein Z1 is OrnN3 and Z2 is Pra.

15. The cyclic peptide of paragraph 1, 2, or 4, wherein Z1 is Az4 and Z2 is absent.

16. The cyclic peptide of paragraph 1, 2, or 4, wherein Z1 is Az4 and Z2 is Pra.

17. The cyclic peptide of any one of paragraphs 1-16, wherein L is 1,4-triazole or 1,5-triazole.

18. The cyclic peptide of any one of paragraphs 1-16, wherein L is 1,4-substituted-1,2,3-triazole (Tz4) or a 1,5-substituted-1,2,3-triazole (Tz5).

19. The cyclic peptide of paragraph 18, wherein L is 1,4-substituted-1,2,3-triazole residue (Tz4).

20. The cyclic peptide of paragraph 18, wherein L is 1,5-substituted-1,2,3-triazole residue (Tz5).

21. The cyclic peptide of any one of paragraphs 1-20, wherein when m is 1, B is a spacer group, a detection tag, or a combination of a spacer group and a detection tag.

22. The cyclic peptide of paragraph 21, wherein the spacer group is polyethylene glycol (PEG) or 6-aminohexanoic acid (Ahx).

23. The cyclic peptide of paragraph 21, wherein the detection tag is an affinity tag, a fluorescent tag, or a fluorescently labeled affinity tag.

24. The cyclic peptide of paragraph 21, wherein the detection tag is selected from the group consisting of biotin, streptavidin, poly-histidine, poly-arginine, FLAG, cyclodextrin, adamantane, copper-DOTA, biotin-PEG3, aminooxyacetate, $^{19}$FB, $^{18}$FB, FITC-PEG$_3$, $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{76}$Br, and combinations thereof.

25. The cyclic peptide of paragraph 21, wherein the spacer group is PEG and the detection tag is biotin.

26. The cyclic peptide of any one of paragraphs 1-25, wherein V1-V2-V3-V4-V5 is not the sequence LRGDGnf (SEQ ID NO:5) or LRGDF-Br (SEQ ID NO:19).

27. The cyclic peptide of any one of paragraphs 1-25, wherein V1-V2-V3-V4-V5 is not the sequence LRGDGnf (SEQ ID NO:5), LRGDF-Br (SEQ ID NO:19), NDETY (SEQ ID NO:25), PSEEG (SEQ ID NO:26), SEEGG (SEQ ID NO:27), EGTGT (SEQ ID NO:28), YEQGE (SEQ ID NO:29), YGEQE (SEQ ID NO:30), LRGDR (SEQ ID NO:31), QEKPP (SEQ ID NO:32), ELTFG (SEQ ID NO:33), VRGDR (SEQ ID NO:34), LRGPR (SEQ ID NO:35), LRGER (SEQ ID NO:36), L(homoR)GDR (SEQ ID NO:37), LRGD(homoR) (SEQ ID NO:38), LGnfGDR (SEQ ID NO:41), LRGAGnf (SEQ ID NO:42), LRGNR (SEQ ID NO:43), LRGQR (SEQ ID NO:44), or LRGAR (SEQ ID NO:45).

28. A method of inhibiting KRAS (G12D) oncogenic protein in a cancer cell expressing KRAS (G12D) oncogenic protein, the method comprising incubating the cancer cell with the cyclic peptide of any one of paragraphs 1-25.

29. The method of paragraph 28, wherein the cancer cell is a pancreatic, colorectal, lung, biliary tract, or ovarian cancer cell.

30. The method of paragraph 28 or 29, wherein the cancer cell is in a subject, wherein the incubation is accomplished by administering the composition to the subject.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Throughout this specification the word "comprise," or variations such as "comprises" or "comprising," will be understood to imply the inclusion of a stated element, integer or step, or group of elements, integers or steps, but not the exclusion of any other element, integer or step, or group of elements, integers or steps.

It must be noted that as used herein and in the appended claims, the singular forms "a," "an," and "the" include plural reference unless the context clearly dictates otherwise. Thus, for example, reference to "a cyclic peptide" includes a plurality of such cyclic peptides, reference to "the cyclic peptides" is a reference to one or more cyclic peptides and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different ligands does not indicate that the listed ligands are obvious one to the other, nor is it an admission of equivalence or obviousness.

Every ligand or cyclic peptide disclosed herein is intended to be and should be considered to be specifically disclosed herein. Further, every subgroup that can be identified within this disclosure is intended to be and should be considered to be specifically disclosed herein. As a result, it is specifically contemplated that any ligand or cyclic peptide, or subgroup of ligands or cyclic peptides can be either specifically included for or excluded from use or included in or excluded from a list of ligands or cyclic peptides.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a cyclic peptide is disclosed and discussed and a number of modifications that can be made to a number of molecules including the cyclic peptide are discussed, each and every combination and permutation of cyclic peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

I claim:

1. A cyclic peptide that selectively binds KRAS (G12D) oncogenic protein, wherein the cyclic peptide is represented by Formula I:

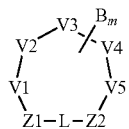

wherein:

Z1 and Z2 are each independently absent, aminoazidobutanoic acid (Az2), azidoornithine (OrnN3), L-azidolysine (Az4), or L-propargylglycine (Pra);

V1 is Q or L, V2 is Q or R, V3 is guanidinophenylalanine (Gnf) or G, V4 is absent or D, V5 is Gnf or bromophenylalanine (F-Br), wherein if V1 is L, V2 is R, V3 is G, and V4 is D, then V5 is not Gnf;

L is a linker; and $B_m$ is an optional group, wherein m is 0 or 1.

2. The cyclic peptide of claim 1, wherein V1-V2-V3-V4-V5 is the sequence QQGnfGnf (SEQ ID NO:3), LRGGnf (SEQ ID NO:4), LRGF-Br (SEQ ID NO:6), LQGnfGnf (SEQ ID NO:7), QRGnfGnf (SEQ ID NO:8), QQGGnf (SEQ ID NO:9), QQGnfF-Br (SEQ ID NO:10), QRGGnf (SEQ ID NO:11), LQGGnf (SEQ ID NO:12), LRGnfGnf (SEQ ID NO:13), QQGDGnf (SEQ ID NO:15), QRGDGnf (SEQ ID NO:16), LQGDGnf (SEQ ID NO:17), LRGnfDGnf (SEQ ID NO:18), LRGDF-Br (SEQ ID NO:19), QQGF-Br (SEQ ID NO:20), QRGF-Br (SEQ ID NO:21), LQGF-Br (SEQ ID NO:22), or LRGnfF-Br (SEQ ID NO:23).

3. The cyclic peptide of claim 1, wherein Z1 and Z2 are both absent.

4. The cyclic peptide of claim 1, wherein when Z1 is Az2, OrnN3, Az4, or Pra, Z2 is absent and when Z2 is Az2, OrnN3, Az4, or Pra, Z2 is absent.

5. The cyclic peptide of claim 1, wherein Z1 is absent and Z2 is Az2.

6. The cyclic peptide of claim 1, wherein Z1 is Pra and Z2 is Az2.

7. The cyclic peptide of claim 1, wherein Z1 is absent and Z2 is OrnN3.

8. The cyclic peptide of claim 1, wherein Z1 is Pra and Z2 is OrnN3.

9. The cyclic peptide of claim 1, wherein Z1 is absent and Z2 is Az4.

10. The cyclic peptide of claim 1, wherein Z1 is Pra and Z2 is Az4.

11. The cyclic peptide of claim 1, wherein Z1 is Az2 and Z2 is absent.

12. The cyclic peptide of claim 1, wherein Z1 is Az2 and Z2 is Pra.

13. The cyclic peptide of claim 1, wherein Z1 is OrnN3 and Z2 is absent.

14. The cyclic peptide of claim 1, wherein Z1 is OrnN3 and Z2 is Pra.

15. The cyclic peptide of claim 1, wherein Z1 is Az4 and Z2 is absent.

16. The cyclic peptide of claim 1, wherein Z1 is Az4 and Z2 is Pra.

17. The cyclic peptide of claim 1, wherein L is 1,4-triazole or 1,5-triazole.

18. The cyclic peptide of claim 1, wherein L is 1,4-substituted-1,2,3-triazole (Tz4) or a 1,5-substituted-1,2,3-triazole (Tz5).

19. The cyclic peptide of claim 18, wherein L is 1,4-substituted-1,2,3-triazole residue (Tz4).

20. The cyclic peptide of claim 18, wherein L is 1,5-substituted-1,2,3-triazole residue (Tz5).

21. The cyclic peptide of claim 1, wherein when m is 1, B is a spacer group, a detection tag, or a combination of a spacer group and a detection tag.

22. The cyclic peptide of claim 21, wherein the spacer group is polyethylene glycol (PEG) or 6-aminohexanoic acid (Ahx).

23. The cyclic peptide of claim 21, wherein the detection tag is an affinity tag, a fluorescent tag, or a fluorescently labeled affinity tag.

24. The cyclic peptide of claim 21, wherein the detection tag is selected from the group consisting of biotin, streptavidin, poly-histidine, poly-arginine, FLAG, cyclodextrin, adamantane, copper-DOTA, biotin-PEG3, aminooxyacetate, $^{19}$FB, $^{18}$FB, FITC-PEG$_3$, $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C, $^{76}$Br, and combinations thereof.

25. The cyclic peptide of claim 21, wherein the spacer group is PEG and the detection tag is biotin.

26. The cyclic peptide of claim 1, wherein V1-V2-V3-V4-V5 is not the sequence LRGDGnf (SEQ ID NO:5) or LRGDF-Br (SEQ ID NO:19).

27. The cyclic peptide of claim 1, wherein V1-V2-V3-V4-V5 is not the sequence LRGDGnf (SEQ ID NO:5), LRGDF-Br (SEQ ID NO:19), NDETY (SEQ ID NO:25), PSEEG (SEQ ID NO:26), SEEGG (SEQ ID NO:27), EGTGT (SEQ ID NO:28), YEQGE (SEQ ID NO:29), YGEQE (SEQ ID NO:30), LRGDR (SEQ ID NO:31), QEKPP (SEQ ID NO:32), ELTFG (SEQ ID NO:33), VRGDR (SEQ ID NO:34), LRGPR (SEQ ID NO:35), LRGER (SEQ ID NO:36), L(homoR)GDR (SEQ ID NO:37), LRGD(homoR) (SEQ ID NO:38), LGnfGDR (SEQ ID NO:41), LRGAGnf (SEQ ID NO:42), LRGNR (SEQ ID NO:43), LRGQR (SEQ ID NO:44), or LRGAR (SEQ ID NO:45).

28. A method of inhibiting KRAS (G12D) oncogenic protein in a cancer cell expressing KRAS (G12D) oncogenic protein, the method comprising incubating the cancer cell with the cyclic peptide of claim 1.

29. The method of claim 28, wherein the cancer cell is a pancreatic, colorectal, lung, biliary tract, or ovarian cancer cell.

30. The method of claim 28, wherein the cancer cell is in a subject, wherein the incubation is accomplished by administering the composition to the subject.

* * * * *